(12) United States Patent
Silva Gonzalez et al.

(10) Patent No.: US 8,574,580 B2
(45) Date of Patent: Nov. 5, 2013

(54) MONOCLONAL ANTIBODIES THAT RECOGNIZE NEUROSPHERES OR NEURAL PROGENITOR CELLS

(75) Inventors: Augusto Silva Gonzalez, Madrid (ES); Ignacio Del Valle Torres, Madrid (ES); Leyre García Benzaquen, Madrid (ES)

(73) Assignee: Consejo Superior de Investigaciones Científicas, Madrid (ES)

( * ) Notice: Subject to any disclaimer, the term of this patent is extended or adjusted under 35 U.S.C. 154(b) by 0 days.

(21) Appl. No.: 12/991,163

(22) PCT Filed: Apr. 29, 2009

(86) PCT No.: PCT/ES2009/070130
§ 371 (c)(1),
(2), (4) Date: Jan. 27, 2011

(87) PCT Pub. No.: WO2009/135976
PCT Pub. Date: Nov. 12, 2009

(65) Prior Publication Data
US 2011/0145938 A1    Jun. 16, 2011

(30) Foreign Application Priority Data
May 8, 2008  (ES) .................. 200801324

(51) Int. Cl.
A61K 39/395    (2006.01)
A61K 39/00     (2006.01)
C07K 16/00     (2006.01)
C12P 21/08     (2006.01)

(52) U.S. Cl.
USPC .............. 424/141.1; 424/130.1; 424/142.1; 424/135.1; 424/136.1; 435/70.2; 435/70.21; 530/388.1

(58) Field of Classification Search
None
See application file for complete search history.

(56) References Cited

FOREIGN PATENT DOCUMENTS

JP     2007055965 A     3/2007
WO    WO 2007114634    10/2007

OTHER PUBLICATIONS

Rudikoff et al. Proc. Natl. Acad. Sci. USA 1982 vol. 79: p. 1979.*
Altman et al, J. Comp. Neurol., 124:319-336, 1965.
Alvarez-Buylla et al., Neuron, 41:683-686, 2004.
Alvarez-Buylla et al., Progress in Brain Research, 127:1-11, 2000.
Bedard et al., Developmental Brain Research, 151:159-168, 2004.
Bedard et al., European J. Neuroscience, 16:1917-1924, 2002.
Bonnert et al., European J. Neuroscience, 24:661-675, 2006.
Doetsch et al., Cell, 97:703-716, 1999.
Doetsch et al., Neuron, 36:1021-34, 2002.
Dutton, Dev Neurosci, 22:96-105, 2000.
Lennington et al., Reproductive Biology Endocrinology, 1:99, 2003.
Pencea et al., Experimental Neurology, 172:1-16, 2001.
Ritter et al., Monoclonal Antibodies: Production, Engineering and Clinical Application, Chapter 2, Production of Monoclonal Antibodies, paragraph 2.2.5 (pp. 13, 14), First Edition, New York, Cambridge University Press, 1995.
Vergano-Vera et al., Generation of GABAergic and dopaminergic interneurons from endogenous embryonic olfactory bulb precursor cells, Development, vol. 133, No. 21, 4367-4379, 2006.
Vicario-Abejon et al., Journal of Neuroscience, 23:3, 895-906, 2003.
International Search Report of PCT/ES2009/070130 mailed Jul. 21, 2009.
Written Opinion of PCT/ES2009/070130 mailed Jul. 21, 2009.
International Preliminary Examination Report of PCT/ES2009/070130 issued Nov. 9, 2010.

* cited by examiner

*Primary Examiner* — Chang-Yu Wang
(74) *Attorney, Agent, or Firm* — Merchant & Gould P.C.

(57) ABSTRACT

Method for generating monoclonal antibodies that recognize progenitor cells. Said method comprises immunization of an Armenian hamster with neurospheres obtained from olfactory bulb cells from a 13.5-day mouse embryo and subsequent selection of the antibodies by means of neurosphere flow cytometry in the presence of propidium iodide. The antibodies thus obtained may be of use in the enrichment of cell cultures in progenitor cells, primarily neural progenitor cells.

3 Claims, 8 Drawing Sheets

Effect of NILO antibodies on cell proliferatio

FIG. 8

Effect of NILO antibodies on differentiation

MONOCLONAL ANTIBODIES THAT RECOGNIZE NEUROSPHERES OR NEURAL PROGENITOR CELLS

This application is a National Stage Application of PCT/ES2009/070130, filed 29 Apr. 2009, which claims benefit of Serial No. P200801324, filed 8 May 2008 in Spain and which applications are incorporated herein by reference. To the extent appropriate, a claim of priority is made to each of the above disclosed applications.

The present invention relates to the use of the monoclonal antibodies, called NILO1 and NILO2, which are bound to cell surface markers, with the aim of identifying, isolating and enriching populations with progenitor cells, including progenitor cells of the central nervous system. It also relates to the specific method to obtain the antibodies, to a pharmaceutical composition containing said antibodies and to its uses, including a method to identify the effect of a molecule or drug on progenitor cell populations.

PRIOR ART

With few exceptions, the neuronal populations of the central nervous system (CNS) had been considered as essentially postmitotic and differentiated, without the capacity to be replaced after their death. The confirmation of active neurogenesis processes, mainly in two areas of the adult CNS of all mammals (Altman and Das, 1965. *J Comp Neurol* 124: 319-35; Alvarez-Buylla et al., 2000. *Prog Brain Res* 127: 1-11; Bedard and Parent, 2004. *Brain Res Dev Brain Res* 151: 159-68; Bonnert et al., 2006. *Eur J Neurosci*; Lennington et al., 2003. *Reprod Biol Endocrinol* 1: 99), suggests a potential of the brain to self-regenerate, including the human brain. This offers a promising future for cell replacement therapies and, therefore, for the treatment of neurodegenerative diseases, for which there is still no effective therapeutic approach.

Neural stem cells constitute the origin of all brain cells, the neurones and the glia. The glia cells, initially considered as support cells, include astrocytes, star-shaped cells involved in different functions and oligodendrocytes, which surround the axons with myelin to protect them. The number of neural stem cells is very few in an adult brain, although neurogenesis is maintained throughout the lifetime in mice and probably in humans.

Neural stem cells are mainly concentrated in certain niches of the central nervous tissue which are particularly the subventricular zone (SVZ) of the lateral ventricle (Doetsch et al., 1999. *Cell* 97: 703-16) and the subgranular zone of the hippocampus, under the dentate gyrus. The telencephalic subventricular zone (SVZ) is the main source of neuronal stem cells in adult mice, generating the olfactory bulb neurons (OB) (Álvarez-Buylla et al., 2000. *Prog Brain Res* 127: 1-11; Bedard et al., 2002. *Eur J Neurosci* 16: 1917-24; Doetsch et al., 2002. *Neuron* 36: 1021-34; Dutton and Bartlett, 2000. *Dev Neurosci* 22: 96-105; Pencea et al., 2001. *Exp Neurol* 172: 1-16). The SVZ consists of a thin layer of cells actively proliferating in the adult age, covering the walls of the lateral ventricles. (Doetsch et al., 1999. *Cell* 97: 703-16). Some of these progenitor cells are concentrated in the anterior body of the ventricle, giving rise to the rostral migratory stream (RMS).

Neural stem cells may also derive from the olfactory bulb as a result of the migration of subependymal cells by the rostral migratory stream (Alvarez-Buylla and Lim, 2004. *Neuron* 41: 683-6). These areas are defined as neurogenic given the possibility of obtaining cells in vitro capable of maintaining the self-renewal growing or in a single layer on a substrate coated with tissue or as aggregates of cells known as neurospheres. The neural stem cells may proliferate and keep the capacity for self-renewal if they grow in the appropriate medium supplemented with EFG and basic FGF. The removal of these factors from the medium causes the differentiation in the main neural types, neurones and glia cells (astrocytes and oligodendrocytes).

Pluripotent cells have been isolated from these proliferative zones and they have been cloned and expanded under culture. Under in vitro conditions, or after being transplanted, these cells have the capacity of generating the three main cell types of the central nervous system and, therefore, are classified as neural pluripotent cells.

The functional substitution of specific neuronal populations by means of the transplant of neural tissue represents a therapeutic strategy that is attractive for treating neurodegenerative diseases. However, neural stem cells are currently obtained from brain tissue by means of tissue biopsy or necropsy, which poses ethical problems and problems of immunological compatibility. Therefore, there still exists the need to provide a source of neural stem cells which overcomes said drawbacks.

In this sense, monoclonal antibodies are known which identify neural stem cells using antigens present inside the cell (intracytoplasmic antigens), which have the drawback that they may not be used in selecting viable cell populations, since they make it necessary to permeabilize the cytoplasmic membrane with the consequent cell death, for which purpose the antibody may be bound to its antigen which is inside the cell. There are many intracytoplasmic monoclonal antibodies that characterize neural precursor cells, such as nestin, Sox2, Vimentin, or GFAP (for very immature precursors) and doublecortin, PSA-NCAM, Ki67, and $\beta$III-tubulin (for proliferative precursors and neuroblasts), but to date only a few antibodies to the surface antigens of the neural progenitor cells have been characterized.

Loss of neural tissue has been proposed as the cause of some neurodegenerative pathologies which entail a progressive loss in brain response and the death of the individual. Today, there are no treatments to cure these diseases and only certain palliative treatments achieve temporary improvements of the disease. One of the reasons for this situation of temporary cure is due to the impossibility of supplying them to these patients by means of the transplant of new neural stem cells, a cell therapy that allows them to regenerate, at least in part, the damaged tissue and improve their situation, probably definitively.

But until today, it has been practically impossible to obtain tools that allow the purification of stem cells for later enrichment, selection and study or use as therapeutic agents, which clearly indicates the need to find new surface markers against neural cells.

EXPLANATION OF THE INVENTION

There is, therefore, the need to find a tool which makes it possible to detect progenitor cells for the enrichment of populations of stem cells and early precursors, which would allow their study and use as therapeutic agents.

In this sense and in accordance with a first aspect of the present invention, a method is provided for generating monoclonal antibodies that specifically recognize membrane antigens of progenitor cells comprising:
   a. generation of neurospheres containing neural stem cells (NSC) from the olfactory bulb of a 13.5 day old mouse embryo.

b. immunization of a 4-month old male Armenian hamster with viable neurosphere cells
c. obtaining the lymphocytes by means of the extraction of the spleen of said animal
d. fusion of the lymphocytes with non-producing mouse myeloma cells, giving rise to hybrid cells or hybridomas
e. determination and/or selection of the antibodies produced by the hybridomas by means of neurosphere cell flow cytometry, wherein the dead cells are excluded from the analysis, in the presence of propidium iodide.

In accordance with a second aspect of the present invention, monoclonal antibodies are provided, obtained by the previous process, comprising:
a) the monoclonal antibody, called NILO1 (clone 1 B6.2.13), produced by the hybridoma deposited on 12 Mar. 2008 with access number DSM No. ACC2887 in the international deposit authority Deutsche Sammlung von Mikroorganismen und Zellkulturen GmbH (DSMZ), Braunschweig, Germany.
b) the monoclonal antibody, called NILO2 (clone 2 B7.10), produced by the hybridoma deposited on 4 Feb. 2008 under access number DSM No. ACC2881 in the international deposit authority Deutsche Sammlung von Mikroorganismen und Zellkulturen GmbH, (DSMZ), Braunschweig, Germany.

A third aspect of the present invention consists of the active fragment(s) of any of the monoclonal antibodies of neural derivative cells.

In accordance with another aspect of the present invention a genetic construction of RNA or DNA is provided capable of transcribing to an antibody or fragment(s) of antibody(ies) of the invention, according to any of the preceding claims.

Said genetic construction, would direct the in vitro or intracellular transcription of the sequence or sequences of the antibody or antibodies (NILO1 and/or NILO2) or fragment or fragments thereof, of the invention, and comprises, at least, one of the following types of sequences: a) sequence of nucleotides, preferably double chain, comprising, at least, the encoding sequence of an antibody of the invention or of the fragment of antibody of the invention for its transcription, b) sequence of nucleotides, preferably double chain, corresponding to a gene expression system or vector comprising the encoding sequence of the sequence of an antibody or fragment of antibody of the invention operationally bound with, at least, one promoter that directs the transcription of said sequence of nucleotides of interest, and with other sequences necessary or appropriate for their suitable transcription and regulation in proper time and correct form, for example, starting and end signals, section sites, polyadenylation signal, replication origin, enhancers, silencers, etc. Multiples of these expression systems or vectors may be obtained by conventional methods known by persons skilled in the art (Sambrook et al., 1989) and form part of the present invention.

Another aspect of the present invention consists of the hybridomas that produce the monoclonal antibodies NILO1 and NILO2, deposited under access number DSM No. ACC2887 and DSM No. ACC2881 in the international deposit authority Deutsche Sammlung von Mikroorganismen and Zellkulturen GmbH, (DSMZ), Braunschweig, Germany.

Another aspect of the present invention describes a method for producing a population highly enriched in stem or progenitor cells comprising:
a) Put in contact a population of cells with a reagent that recognizes an epitope or antigenic determinant in a cell surface marker recognized by the monoclonal antibody NILO1 and/or the monoclonal antibody NILO2; and
b) Selecting the cells wherein there is a contact between the reagent and the epitope or antigenic determinant.

In a preferred embodiment of the present invention, the stem cells are stem cells from the human central nervous system that may initiate neurospheres (NS-IC).

In a more preferred embodiment of this aspect of the invention, the population containing neural cells or neural derivative cells is obtained from a culture of neurospheres.

In a more preferred embodiment of this aspect of the invention, the reagent is selected from a list comprising:
a) an antibody, or fragment thereof, capable of recognising an epitope or determinant in the cell surface marker recognized by the monoclonal antibody NILO1,
b) an antibody, or fragment thereof, capable of recognising an epitope or determinant in the cell surface marker recognized by the monoclonal antibody NILO2,
c) a NILO1 antibody or active fragments thereof.
d) a NILO2 antibody or active fragments thereof.
e) a ligand or a molecule which binds to the surface marker recognized by the NILO1 antibody,
f) a ligand or a molecule which binds to the surface marker recognized by the NILO2 antibody,
g) a fluorochrome conjugate,
h) a conjugate with magnetic particles.

In an even more preferred embodiment of this aspect of the invention the reagent contains the monoclonal antibody NILO1 and/or NILO2, coupled to markers such as enzymes, chromophores, chemiluminescent materials, radionucleotides or nanoparticles.

In an even more preferred embodiment of the present invention, the selection of the progenitor cells is performed by means of flow cytometry techniques, FACS flow cytometry (Fluorescence-activated cell sorting), or of microscopy, or using immunocytochemistry techniques (cells) or immunohistochemistry techniques (tissue), or by magnetic selection, or by any another positive selection method.

Another aspect of the present invention provides an enriched population of stem cells or neural progenitor cells. Said enriched population has been obtained according to the previously described method.

In a preferred embodiment of this aspect of the invention, the population enriched with stem cells or progenitor cells is used as a medicament.

In a more preferred embodiment of this aspect of the invention, the population enriched with stem cells or progenitor cells is used in the treatment of degenerative diseases or disease that occur with tissue destruction processes. These diseases include, but are not limited to, Alzheimer's, Parkinson's, diabetes, cardiovascular necrosis or haematopoietic depletion.

In accordance with another aspect of the present invention, a drug screening or discovery method is described comprising the following steps:
a) selecting from a population containing neural cells or neural derivative cells which are bound to the monoclonal antibody NILO1 and/or al monoclonal antibody NILO2, and in this way producing an enriched population for human neurosphere initiator cells (NS-IC) if compared with the population of neural cells or neural derivatives,
b) inoculating in a non-human mammal said enriched population,
c) administering a composition with pharmaceutical potential to said mammal as well as to another non-human mammal which has not been inoculated with the population described in the preceding phase (control subject); and d) comparing the effect of said administration between both mammals.

In a preferred embodiment of the present invention, the non-human mammal is a rodent.

In accordance with another aspect of the present invention, a drug screening or discovery method is described comprising the following steps:
  a) selecting from a population containing neural cells or neural derivative cells which are bound to the monoclonal antibody NILO1, and further enriching said population by additional selection of the cells which are bound to the monoclonal antibody NILO2, and in this way producing an enriched population for human neurosphere initiator cells (NS-IC) if compared with the population of neural cells or neural derivatives,
  b) inoculating in a non-human mammal said enriched population for human CNS-SC that may initiate neurospheres (NS-IC)
  c) administering a composition with pharmaceutical potential to said mammal as well as to another non-human mammal which has not been inoculated with the population described in the preceding phase (control subject); and
  d) comparing the effect of said administration.

In a preferred embodiment of this aspect of the invention a method like the above is described, wherein the non-human mammal is a rodent.

DEFINITIONS

The term "antibody" as used in this specification, relates to immunoglobulin molecules and immunologically active portions of immunoglobulin molecules, i.e. molecules containing an antigen fixation site specifically bound (immunoreacts with) to a surface marker or an epitope. Examples of portions of immunologically active immunoglobulin molecules, include fragments F(ab) and F(ab')2 which may be generated treating the antibody with an enzyme such as pepsin.

The expression "monoclonal antibody" or "monoclonal antibody composition" as used in this specification, alludes to a population of antibody molecules containing only one kind of antigen fixation site capable of immunoreacting with a particular epitope of the progenitor cells. A monoclonal antibody composition, therefore, shows a unique binding affinity for the progenitor cell with which it immunoreacts. Conventional antibodies, or "polyclonal antibodies", typically include different antibodies directed against different determinants (epitopes), whilst each monoclonal antibody is directed against a single epitope in the antigen.

The term "epitope" in this specification relates to the part of a macromolecule recognized by the immune system, specifically by antibodies, B cells, or T cells. Although it is usually thought that epitopes are derived from proteins that are not their own, the sequences derived from the host may be recognized and also classified as epitopes.

Using recombinant DNA technology, it is possible to construct an antibody binding the variable or antigenic recognition region to a framework of a human antibody. Thus, the monoclonal antibody may be biochemically altered by genetic manipulation or may be synthetic, possibly lacking the antibody in its totality or in parts, of portions that are not necessary for the recognition of the progenitor cell and being substituted by another which communicate additional advantageous properties to the antibody.

A "recombinant antibody" is one which has been produced in a host cell which has been transformed or transfected with the nucleic acid coding for the antibody, or produces the same as a result of the homologous recombination.

"Transformation" and "transfection" are interchangeably used to relate to the process of introducing the nucleic acid in a cell. After the transformation or transfection, the nucleic acid can be integrated in the genome of the host cell or may exist as an extrachromasomal element. The "host cell" includes a cell in an in vitro culture as well as a cell in a host animal. U.S. Pat. No. 5,534,615 discloses, for example, some of these processes for the recombinant production of polypeptides.

It is said that a cell has been "genetically altered", "transfected" or "genetically transformed" when a polynucleotide has been transferred to a cell by any available method by means of artificial manipulation, or when the cell is the progeny of the originally altered one which inherently has the transferred polynucleotide. The polynucleotide may often comprise a sequence which can be transcribed and which encodes a protein of interest, which enables the cell to express said protein. Genetic alteration is said to be "inheritable" if the progeny of the altered cell have the same alteration.

The antibodies may also be "chimerical", immunoglobulins wherein a region of the heavy and/or light chain is identical to or homologous with the corresponding antibody sequences from a determined species or belonging to a class or subclass of determined antibodies, whilst the remaining chain(s) are identical to or homologous with the corresponding sequences in antibodies derived from other species or belonging to another class or subclass of antibodies, as well as fragments of said antibodies, so that they demonstrate the desired biological activity (U.S. Pat. No. 4,816,567).

The term "hypervariable region" when used in the present document, relates to residues of amino acids of an antibody responsible for the bond to the antigen. The hypervariable region comprises residues of amino acids of a "complementarity determining region" and/or those residues of a "hypervariable loop". The framework residues or "FR" are those residues of the variable domain different from the residues of the hypervariable region, as defined in the present document.

In most cases, the humanized antibodies are human immunoglobulins (receptor antibodies) wherein the residues of the hypervariable regions of the receptor have been substituted by residues of a hypervariable region of a non-human species (donor antibody) such as mouse, rat, rabbit or a non-human primate which has the desired specificity, affinity and capacity.

In some cases, the framework residues (FR) of the Fv region of human immunoglobulin are substituted by the corresponding non-human residues. Furthermore, the humanized antibodies may comprise residues not found in the receptor antibody or in the donor antibody. These modifications are performed to further refine antibody function. In general, the humanized antibody shall substantially comprise all of at least one, and generally two, variable domains, wherein all or practically all of the hypervariable loops correspond to those of a non-human immunoglobulin and all or substantially all the FR regions are those of a sequence of human immunoglobulin. The humanized antibody will also optionally comprise at least part of a constant region of the immunoglobulin (Fc), in general of a human immunoglobulin. Different processes to obtain humanized antibodies are known in the state of the art.

The "fragments of antibodies" comprise at least part of a full length antibody, generally the antigen binding region or variable thereof. Examples of fragments of antibodies include the Fab, Fab', F(ab')$_2$ and Fv fragments; diabodies; linear antibodies; single chain antibody molecules; and multispecific antibodies formed by fragments of antibodies. Several techniques have been developed to produce fragments of antibodies. Traditionally, these fragments come from the proteolytic digestion of intact antibodies. However, these fragments can now be produced directly by means of recombinant host cells. For example, the fragments of antibodies can be isolated from the libraries of antibody phages. Alternatively, the Fab'-SH fragments can be directly recovered from *E. coli* and chemically bound to form F(ab')2 fragments. In another embodiment, the F(ab')2 is formed using the leucine zip GCN4 to promote the assembly of the F(ab')2 molecule. In accordance with another approach, the F(ab')2 fragments of the recombinant host cell culture can be directly isolated. Other techniques for the production of fragments of antibodies shall be evident for persons skilled in the art. In other embodiments, the chosen antibody is a single chain Fv fragment (scFv). For a revision, see WO/1993/016185.

"Single chain Fv" (scFv) or "fragments of antibodies" comprise the VH and VL domains of the antibody, wherein these domains are present in a single polypeptide chain. In general, the Fv polypeptide further comprises a polypeptide setting between the VH and VL domains which enables the desired structure for the antigen binding to be formed.

The term "diabodies" relates to small fragments of antibodies with two antigen binding sites, these fragments comprising a heavy chain variable domain (VH) connected to a light chain variable domain (VL) in the same polypeptide chain. Using a setting that is too short to allow the two domains to pair in the same chain, the domains are forced to pair up with the complementary domains of another chain and create two antigen binding sites.

The expression "linear antibodies" relates to antibodies comprising a pair of tandem segments Fd (VH-CH1-VH-CH1) which form a pair of antigen binding regions. The linear antibodies may be bispecific or monospecific.

"Multispecific antibodies" have binding specificities for at least two different epitopes wherein the epitopes are normally of different antigens. Whilst said molecules are normally bound to only two antigens (i.e. bispecific antibodies, BsAbs), antibodies with additional specificities such as trispecific antibodies, are included within the expression when used in the present document. Processes are known in the state of the art for the preparation of bispecific antibodies. In the present invention the fragments of antibody are capable of specifically binding to an epitope of a progenitor cell.

The term "stem cell" relates to a relatively quiescent non-differentiated cell capable of proliferating and giving rise to more stem cells, also having the ability of generating a large number of progenitor cells that, in turn, may give rise to differentiate cells or differentiated or differentiable daughter cells. They can be self-maintained, which means that with each cell division a daughter cell will also be a stem cell.

The term "neural stem cell" (NSC) relates to multipotential stem cells capable of producing a progeny capable of differentiating neurons, astrocytes and oligodentrocytes.

The term "progenitor cell" relates to an undifferentiated cell derived from a stem cell. The progenitor cell may be self-renewed but has a limited proliferative capacity (unlike a stem cell, the proliferation capacity is limited and, therefore, does not exhibit self-maintenance). It is committed to a particular differentiation route and, possibly, in appropriate conditions, to differentiate neurones, astrocytes or oligodendrocytes.

The term "precursor cells" relates to the live cells modified or manipulated by means of the methods of the invention as soon as they are derived from stem cells, in vivo or in vitro, and include both progenitor cells and stem cells, therefore being self-renewable and multipotent. In vitro, the precursor cells derived from neural stem cells typically grow in the form of neurospheres, but they may exhibit different growth patterns depending on culture conditions.

The term "neurosphere" relates to a grouping of cells derived from neural stem cells and cultured in vitro. At least some of the cells are of the nestin phenotype (+) (that react with the nestin, intracytoplasmic marker of neural stem cells). The grouping is composed of stem cells and/or progenitor cells, and may or may not include differentiated cells.

The preferred source of neuronal tissue is obtained from mammals, preferably rodents (for example, mice and rats) and primates, the most preferred ones being from humans (excluding human embryonic tissues). U.S. Pat. Nos. 5,750,376 and 5,851,832 disclose a method for the isolation and proliferation of self-renewable and multipotential CNS neuronal stem cells from adult human neuronal tissue, from adult Rhesus monkey, from mouse embryo, and from brain tissue from juvenile and adult mice. The method includes establishing neuronal stem cells in the culture from neuronal stem cells of the CNS, as well as the differentiation of the progeny of the CNS neuronal stem cell.

The term "ventricle" relates to any cavity or conduct within the central nervous system where through the cerebrospinal fluid flows. Thus, the term not only includes lateral, third and fourth ventricles, but also includes the central channel and cerebral aqueduct.

The term "ventricular tissue" relates to the tissues that cover the CNS ventricles and include the subependymal zone comprising a collection of undifferentiated cells including the stem cells of the CNS and the progenitor cells.

The term "constitutive proliferative population" relates to the population of cells that are divided located within the subependymal zone of the lateral ventricles of the anterior brain in adult mammals [as outlined by Smart; J. Comp. Neurol. 116:325, (1961)], and approximately comprises 33% of the cells in some regions of the subependymal zone [Morshead and van der Kooy, *J. Neurosci.* 12:249, (1992)].

Throughout the description and the claims, the word "comprises" and its variants do not aim to exclude other technical characteristics, additives, components or steps. For persons skilled in the art, other objects, advantages, and characteristics of the invention shall be partly gathered from the description and partly from practice of the invention. The following examples and drawings are provided by way of illustration and do not aim to be limiting of the present invention.

DESCRIPTION OF THE FIGURES

From the olfactory bulb of 13.5 day embryo, neurospheres are generated which, in run 5-6 are used as antigens to immunize an adult Armenian hamster (*Cricetulus migratorius*) with three injections of 5 million cells during three months. Three days after the last immunization, the spleen cells are fused with the non-producing myeloma of Balb/c P3-X63.Ag8.653. The clones selected in HAT, grow and are analysed via flow cytometry.

a) The monoclonal antibodies that mark with a certain intensity cells derived from neurospheres of the olfactory bulb of 13.5 day old mice and neurospheres derived from the SVZ of 6-week old adult mice are selected by flow cytometry. The cytometry was performed in a Coulter XL; 10,000 events were run selecting those with cellular morphology and which were not stained with propidium iodide, to exclude the dead cells, b) Marking of neural tissue cells derived from the SVZ of six week old mice, for NILO1 or NILO2, and after its different runs in cell culture as neurospheres.

a) The neurospheres were simultaneously marked with nestin and with a FITC anti-mouse polyclonal secondary antibody and with NILO1 using a secondary anti-hamster marked with Cy5. b) the same as a) but marking with anti-GFAP, NILO1 and DAPI (nuclei), c) d) and e) neurospheres in MATRIGEL®, a gelatinous protein mixture secreted by Engelbreth-Holm-Swarm (EHS) mouse sarcoma cells, marked with NILO2.

a) and c) NILO1 with GFAP at different magnifications; b) and d) NILO2 with GFAP a different magnifications; e) NILO1 and nestin; f) NILO1 and Ki67.

Tissue cryostat sections fixed with paraformaldehyde and stained with NILO1 (green-FITC) and doublecortin (DCX), GFAP, Vimentin, βIII-tubulin (Tuj1), Ki-67 and PSA-NCAM. The monoclonal antibodies are indicated in Table 1.

Tissue cryostat sections fixed with paraformaldehyde and stained with NILO2 (green-FITC) and doublecortin (DCX), GFAP, Vimentin, βIII-tubulin (Tuj1), Ki-67 and PSA-NCAM. The monoclonal antibodies are indicated in Table 1.

The cells are incubated with NILO2 and later used with lysis buffer in the presence of 5% Brig58 (Sigma). The purified extracts are developed with different methods.

The cells are incubated in the presence of the antibody concentrations indicated during 24, 48 and 72 hours and the proliferation measured using the MTS tetrazolium compound to measure proliferation.

The cells are incubated in the presence of neurosphere medium in the absence of FGF2 and EGF and in the presence of 0.5% FCS, which causes a rapid differentiation of the precursor cells to differentiated cells. In the presence of the antibody concentrations indicated during 2 days and 4 days we measure the capacity of cells to proliferate using the MTS tetrazolium to measure the proliferation and their capacity for differentiating or maintaining their neurosphere structure.

a) The bone marrow cells are selected by means of flow cytometry (sorting) using NILO1, or b) are selected by their capacity of adherence and of obtaining mesenchymal cells. c) mesenchymal precursor cells in bone marrow or selected after one week in culture marked with NILO1. d) bone marrow or mesenchymal cells marked with Sca-1, Alpha6, beta1, NILO1 and NILO2, e) NILO1 cells after two weeks in neurosphere medium and f) their differentiation in Tuj1+ cells, or g) NILO1 cells after six weeks in adipocyte differentiation medium (stained with red oil) or h) unstained (grease drops).

A small percentage of cells (<3%) in breast tissue of six week old mice were found to be positive for NILO1. These cells were capable of forming mammospheres (FIG. 11a) and were weakly marked with Sca-1 (FIG. 11b), which suggests the cells are precursor cells. To confirm that the cells were precursor cells, disaggregated breast tissue cells were marked with NILO1 antibody and NILO1+ and NILO1− negative cells were used in transplants of breast precursor tissue in the breast fat of mice. The presence of three-dimensional breast structures were analyzed 8 weeks post-transplant (FIG. 11c). The NILO1 positive cells were capable of reconstituting a three-dimensional breast structure.

DETAILED EXPLANATION OF EMBODIMENTS

Below, the invention will be illustrated by means of assays performed by the inventors revealing the specificity and efficacy of the monoclonal antibodies NILO1 and NILO2.

Example 1

Generation of the Monoclonal Antibodies NILO1 and NILO2

The inventors present a method for obtaining monoclonal antibodies to neural stem cells, which has the use of neurospheres derived from 13.5 day embryonic cells, as a source of antigenic stimulus and the use of Armenian hamsters of less than three months old, as the receptor of the immunizations, via a specific pattern. Obtaining the spleen and its fusion with mouse myeloma cells allows, after the selection in specific selective media of inter-species hybridomas that secrete monoclonal antibodies of hamster origin and with specificity against neural stem cells, both of embryonic origin and neural stem cells from adult animals.

Antigen Used for the Immunization

Neural stem cells (NSC) derived from neurospheres were used. The cells that grow as neurospheres may disaggregate and be cloned in cultures being capable of forming new neurospheres. The cells that form part of the neurospheres are considered neural progenitor cells as they are capable of differentiating into "in vitro" cultures in the different cell types of the brain such as neurones and glia (astrocytes and oligodendrocytes). Furthermore, these cells have defined intracellular markers, such as "nestin", and may be differentiated to cells of any of the neural lines such as neurones, oligodendrocytes or astrocytes.

These NSC may be maintained in a culture through cell dilution runs, although the conditions and peculiarities of the cells in proliferation may change depending on the number of runs which are kept in culture. This protocol, to obtain monoclonal antibodies to these NSC, uses cells in run 3 to 5, run 0 being the time to obtain these cells from the mouse tissue.

There are different brain regions in the adult mouse that may be used to obtain NSC. The most important neurological areas are the subventricular region (SVZ) and the granular region of the dentate gyrus of the hippocampus. However, the efficiency of obtaining NSC in the adult mouse is low, and given that a minimum number of cells are required to carry out the repeated immunizations, our protocol obtains the NSC from embryonic tissue from 13.5 day old mice, specifically the olfactory bulb. It is easy to obtain important amounts of NSC from this tissue, which may be used for immunization.

Animals Used for the Immunization.

To obtain monoclonal antibodies to mouse neural progenitor cells, 4 month old male Armenian hamsters have been used. The animals are kept in animal houses in normal temperature and humidity conditions, as with other mice, although in an independent room and in peaceful conditions. Although Armenian hamsters had also been used to obtain monoclonal antibodies to other mouse antigens, never to date have they been used to generate antibodies to neural components. It is important that Armenian hamsters are used, other hamster subspecies *not* being equally valid.

The animals were immunized with viable disaggregated neurosphere cells, injected in PBS at a concentration of $5 \times 10^6$ cells/ml. The immunization route was always intra-peritoneal, using a hypodermic syringe and in alternate locations in each immunization ("booster"). The immunization guideline was as follows: day 0, 30 days and 60 days. After the third re-immunization with the cells derived from neurospheres, three days were waited and the animal was sacrificed after total anaesthesia to remove the spleen, which will be used to extract the lymphocytes and their later fusion with the myeloma cells.

Cell Fusion

The fusion protocol is similar to that previously described by other authors. Briefly, the lymphocytes derived from the spleen of the hamster immunized with NSC are washed in medium and resuspended in DMEM without serum. The mouse myeloma cells and the cells that are going to be fused are mixed in a 50 ml Falcon tube. We use $10^7$ non-producing myeloma cells from the Balb.c mouse called P3-X63.Ag8.653 and $10^6$ cells from the spleen of the hamster immunized by fusion. The cells were centrifuged together at 1500 r.p.m. for 5 minutes at ambient temperature. The supernatant is eliminated by aspiration to eliminate everything. The tube alone with the cells is placed in a bath at 37° C. 0.4 ml of polyethylene glycol (40% PEG in water) is added drop by drop on the cell suspension for 1 minute with occasional gentle stirring. It was then slowly diluted drop by drop with 5 ml of DMEM medium without serum and previously tempered at 37° C., for a period of no more than 3 minutes. The suspension is gently mixed, it is completed with DMEM-10% FCS complete medium and it is incubated at 37° C. for 30 to 45 min. Then the cells are distributed in 0.1 ml/well in flat-bottomed 96-well plates and they are kept in the incubator at 37° C., 5% CO2. One day after the fusion, 0.1 ml/well of DMEM-10% FCS medium containing HA(2×) was added. The medium is aspired and changed once per week. The hybrids are detected visually or under a low resolution inverted microscope. Three weeks after fusion, the colonies were transferred to 24-well plates with 2 ml of selective medium per well.

Selection of Antibodies with Specificity for Neural Stem Cells.

The selection is made by means of detection of cells positively marked with our antibodies in flow cytometry against NSC cells, derivatives; 1) olfactory bulb neurospheres from 13.5 day old embryos, 2) neurospheres of adult mice; 3) thymus tumour cells from BW5147 mouse, 3) bone marrow cells of adult mice.

The marking is performed using a ½ dilution of the cell culture supernatant. The secondary antibody used is an anti-hamster IgG (cocktail) (Becton Dickinson, Ltd.) marked with different alternatives (FITC fluorochromes, PE or biotin).

The fusion supernatants that mark the neurosphere NSC cells and which were negative for the BW5147 thymoma are expanded and frozen. Approximately 80 antibodies were selected from the 295 hybrids selected. The supernatants selected include the monoclonal antibodies called NILO1 and NILO2.

Example 2

Identification of Neurosphere Cells with the NILO Monoclonal Antibodies

NILO1 and NILO2 are hamster immunoglobulins IgG produced by hybridomas between hamster B lymphocytes and the non-producing myeloma P3-P3-X63.Ag8.653.653 derived from the Balb/c mouse. Despite being an inter-species fusion (hamster×mouse) the stability of the hybridoma is sufficiently high to guarantee its selection and cloning. The monoclonal antibodies produced by the NILO1 and NILO2 hybridomas, may be purified by means of sepharose columns bound to a G-protein or an A-protein, which guarantees their purity and allows their direct marking with different dyes (fluorescein, phycoerythrin, etc). There are currently NILO antibodies marked with FITC and with PE.

The NILO1 and NILO2 antibodies have enormous selectivity for neural stem cells, as shown by the immunocytochemistry, immunohistochemistry and functional studies presented in this specification.

On the other hand, the bonding of these antibodies to magnetic particles has been tested, enabling a rapid purification and in just one run of neural progenitor populations from other sources. This has allowed us to enrich in a single run bone marrow populations which have been used in cell reconstitution experiments. This situation will have great repercussions for cell therapy treatments for degenerative diseases (Alzheimer's, Parkinson's, etc.) or disease which occur with tissue destruction processes and today with enormous repercussion (diabetes, cardiovascular necrosis, haematopoietic depletion, etc.).

Figure 1:
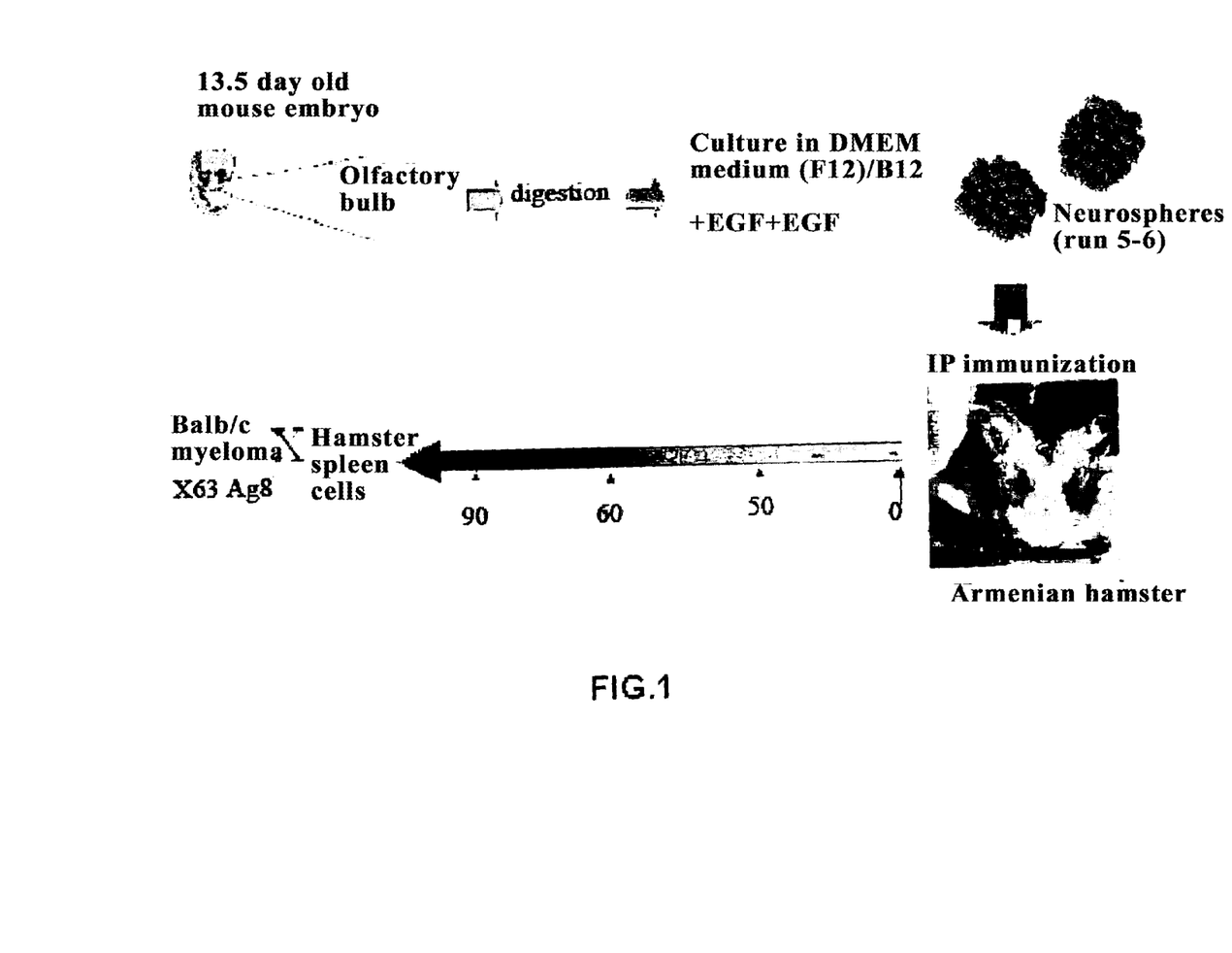
FIG. 1. Diagram describing the origin of NILO hybridomas.
Figure 2:
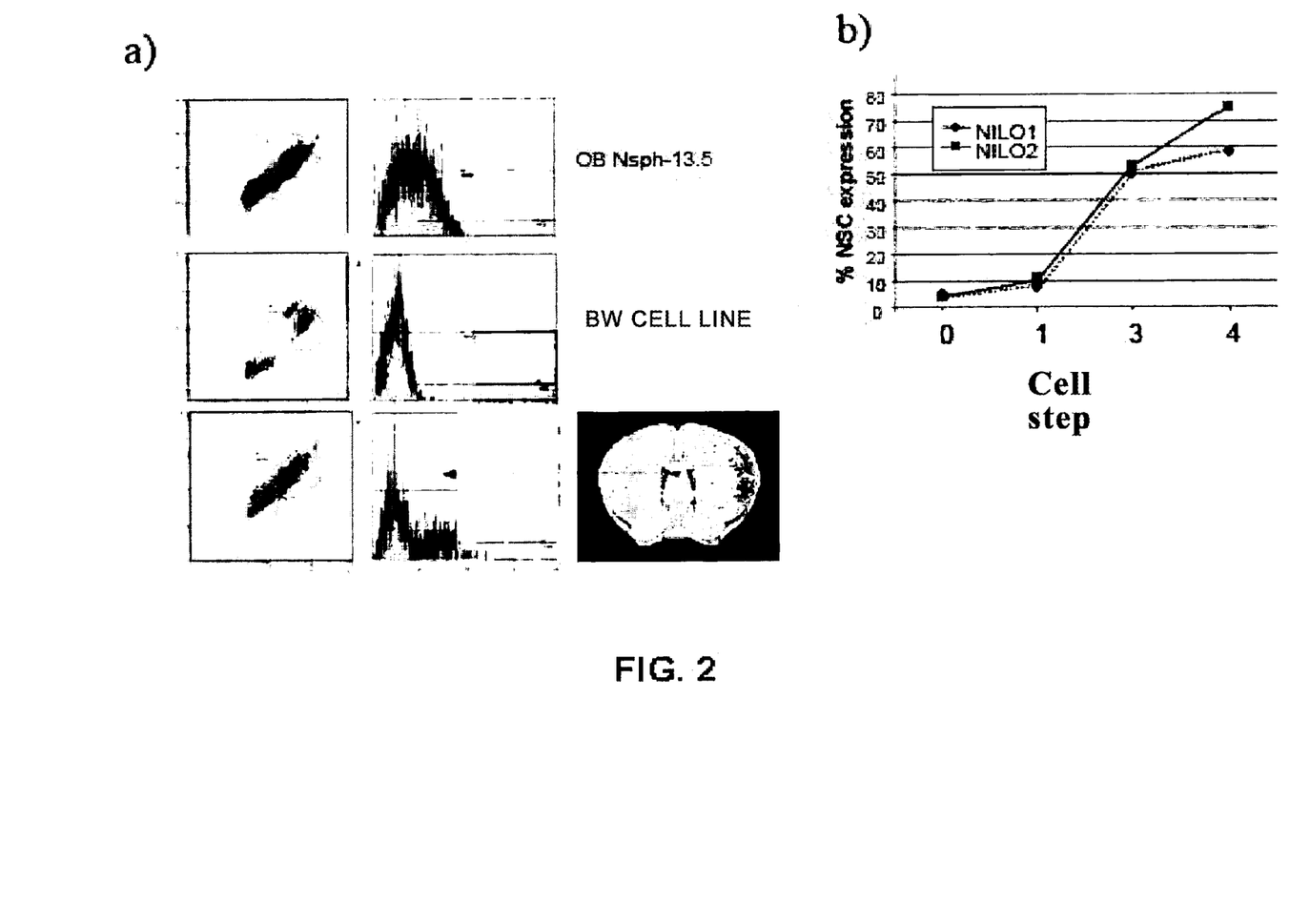
FIG. 2. Diagram of the selection method of monoclonal antibodies.

To demonstrate the great selectivity of the NILO antibodies, different types of experimental designs have been performed. The first study consisted of demonstrating the marking of neurosphere cells, detected by means of flow cytometry. The marking of the cells with these antibodies was carried out in the presence of propidium iodide (10 µg/ml) to exclusively select the negative cells for this DNA marker, which guaranteed the marking of live cells and that the marking was not intracytoplasmic (FIG. 2). The profile and percentage of cells marked by the monoclonal antibodies NILO1 and NILO2 differs between them, which suggests that each antibody is identifying different surface proteins.

Figure 3:
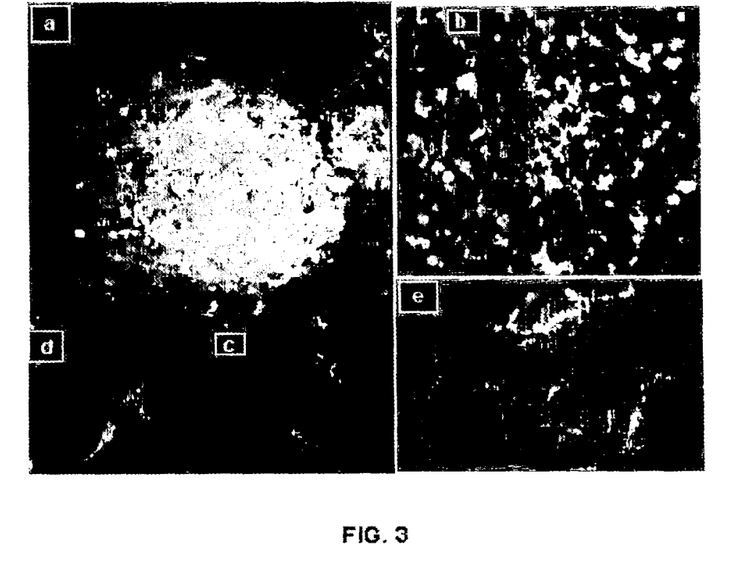
FIG. 3. Marking of neurosphere cells with NILO1 and NILO2 by means of immunocytochemistry.
Figure 4:
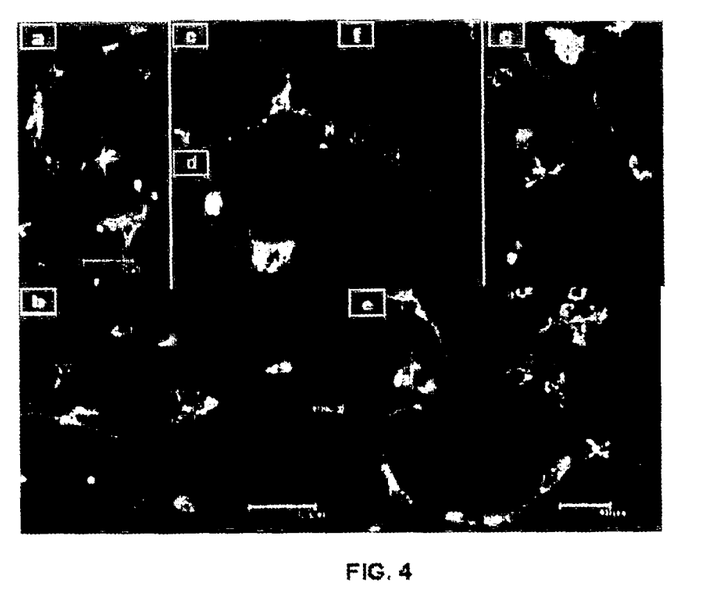
FIG. 4. Double expression of NILO and antibodies that define neural populations in neurosphere cells on MATRIGEL®.

Neurospheres generated from the subventricular region of the brains of adult mice (FIG. 3a), from the olfactory bulb of brains from 13.5 day old mice embryos (FIG. 3b), and from the olfactory bulb of adult mice (FIG. 3c) have been analysed using immunocytochemistry techniques. The neurospheres are marked with double staining using commercial anti-nestin antibody or anti-GFAP antibody. The double marking demonstrates the specificity of the stained cells and their association with the neural stem cell lineage. Furthermore, individual marking was performed on neurosphere cells separated and adhered to the plastic of the culture plates with MATRIGEL®, which allows its more detailed individual analysis. FIG. 4 shows the simultaneous expression of GFAP, nestin and Ki-67 NILO1 or NILO2 on cells in MATRIGEL®. GFAP marks very precursor cells or glia cells. It can clearly be observed that although the staining is unicellular in both cases with GFAP, the marking of GFAP and NILO are localized in different areas and do not coincide within the cell.

In FIG. 3 it is possible to verify the presence of NILO1 cells with the presence of nestin, intracytoplasmic marker of neural stem cells, although, NILO1 marks a cell subpopulation within the nestin+neural progenitor cells.

Example 3

NILO Markers in the SVZ Region of the Brain

NILO antibodies are specific for neural stem cells, as demonstrated by their exclusive presence in neurogenic regions of adult mice brains. Principally, cells positive for NILO have been detected in the SVZ region of adult mice and in the dentate gyrus of the hippocampus.

To demonstrate that the NILO1 and NILO2 cells correspond with neural progenitor cells, we perform an immunohistochemistry study making double markings with doublecortin (DCX), nestin (Nes), GFAP, Vimentin, βIII-tubulin, PSA-NCAM and Ki67, all markers associated with different points in the development of neural cells from neural precursor cells and as figures in the attached Table 1. The histochemistry sections are performed by means of cryostat in semithick sections (30 microns), with the aim of analyzing the sections in detail.

Figure 5:
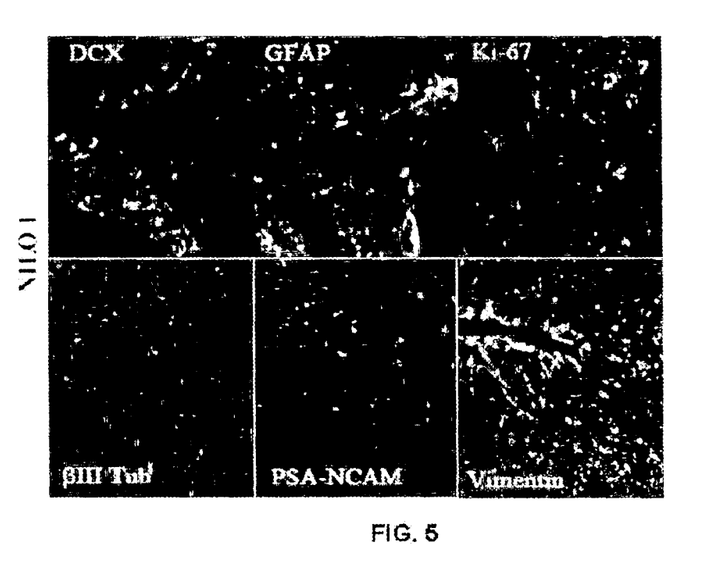
FIG. 5. Marking of brain sections with NILO1 detecting neural progenitor cells in neurogenic region of the SVZ.
Figure 6:
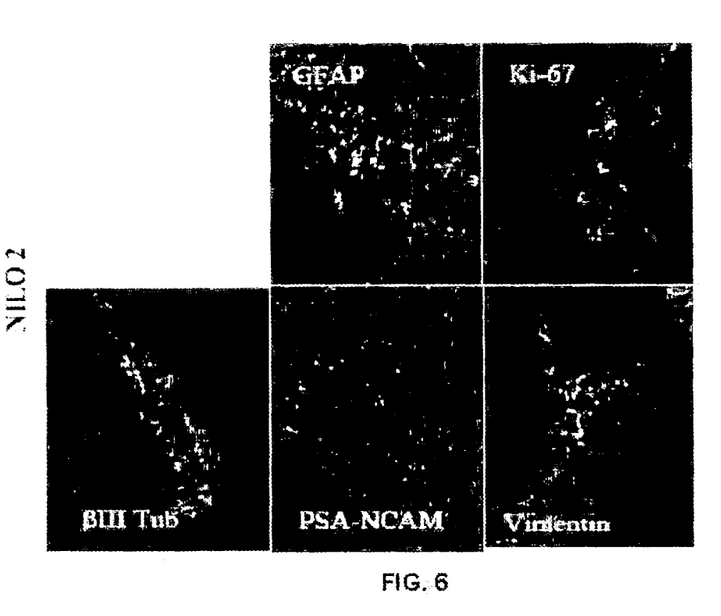
FIG. 6. Marking of brain sections with NILO2 detecting neural progenitor cells in neurogenic regions of the SVZ.
Figure 7:
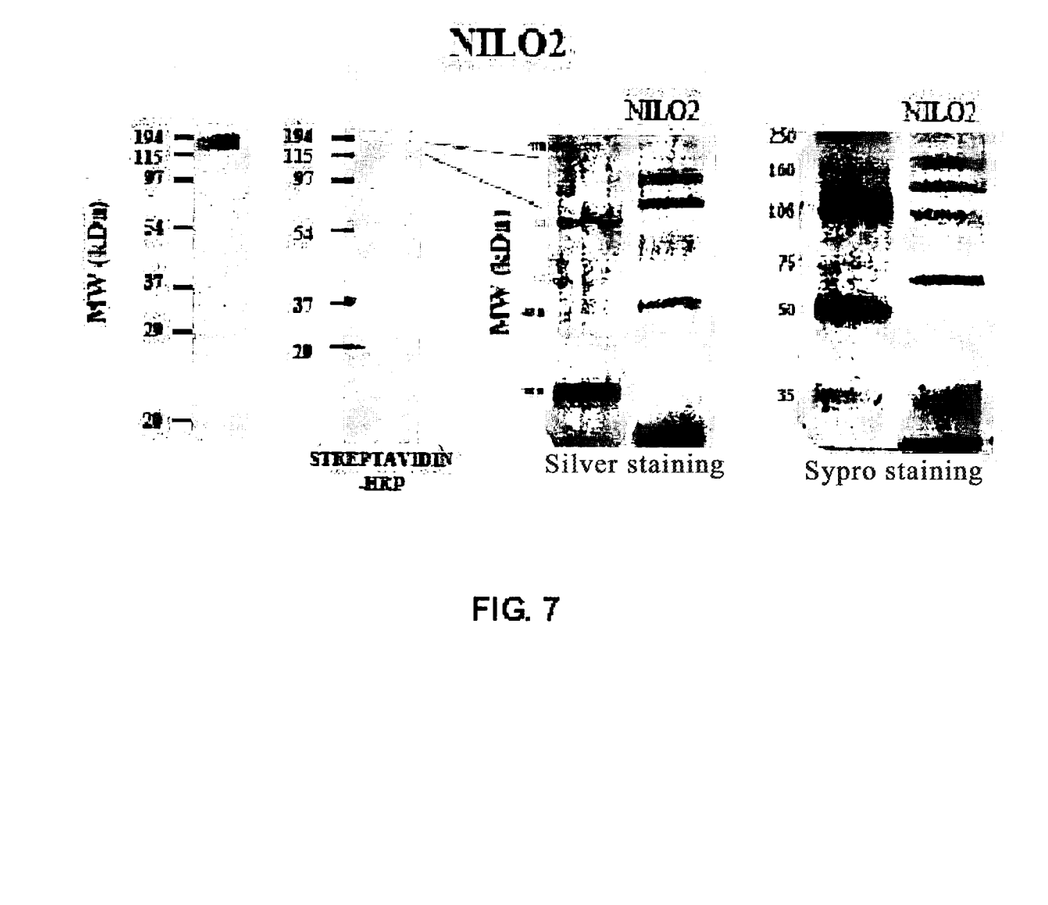
FIG. 7. Surface protein immunoprecipitated by NILO2 in cells derived from neurospheres and in the cell line C2C12.

The data demonstrate that NILO1 (FIG. 5) and NILO2 (FIG. 6) are selective markers of neural progenitor populations identifying progenitor cells in cycle and primitive neuroblasts, since their marking coincides in doubly positive cells for DCX, Ki67, Vimentin, βIII-tubulin, and in proximity with the GFAP marker, which although not directly coincident, as we observe in the histochemistry of the cells in MATRIGEL®, co-localize in very close areas.

the antigens recognized by them. Neural progenitor cells have been used marked on their surface with biotin or alternatively the C2C12 line which is recognized by the NILO2 and NILO2 antibodies. After the marking of the cells with biotin, the antibody is bound and subsequently lysed as described in Material and Methods using the Briji detergent. The proteins immunoprecipitated with NILO2, both in neurosphere cells and in the C2C12 line, have two majority bands of 140 and 170 kD, whilst NILO1 may not be used in "western blot". These data demonstrate that each monoclonal antibody identifies a different type of cell surface protein of the progenitor cells, independent of the similar location of these antibodies by immunohistochemistry. A very relevant situation is that identified by the surface antigen (cell receptor) which is identified by NILO.

Example 5

Functional Effect of the NILO1 and NILO2 Antibodies on the Proliferation and Differentiation of Neurospheres The cell distribution of NILO is homogenous in the neural stem cells. The neural stem cells are maintained in their progenitor condition provided that they are kept under strict cell culture conditions in the presence of growth factors such as fibroblast growth factor 2 (FGF2) and epidermal growth factor (EGF) and in the absence of fetal calf serum (FCS). In the absence of these factors, FGF and EGF, and in the presence of FCS, the cells halt their proliferation and differentiate in any of the neural lineage cells: neurones, oligodendrocytes or astrocytes.

The possible functional effect of the NILO antibodies on the proliferation of neural progenitor cells has been researched. Using the NILO1 and NILO2 antibodies it has

TABLE 1

Markers used to detect the presence of NILO in cells and neurogenic regions

| Marker | Commercial reference | Marker characteristics | Publications |
|---|---|---|---|
| Nestin | MAB353 Chemicon | Intermediate filament present in quiescent and proliferative neural progenitors and in neurosphere cells. Negative in neuroblasts. | Niu S et al. Neuron 2005. 41 |
| Glial fibrillary acid protein (GFAP) | | Present in radial glial and in very early precursors | Viale et al. Arch A Pathol. Anat. 1991. 418 |
| Vimentin | Ab7783 AbCam | Present in quiescent early progenitors | Husse B and Isenberg G. BBRC 2005. 334 |
| Polysialic acid-Neural Cell Adhesion (PSA-NCAM) | Chemicon MAB5324 | Present in neuroblasts 1 and 2 and in immature neurons. Negative in early quiescent precursors and in mature neurons. | Theodosis D et al. 1999. J. Neuroscience. 19. Rougon G et al. 1982. EMBO J. 1 |
| Doublecortin (DCX) (C-18) | Sc-8066 SantaCruz | Type 1 and 2 neuroblasts and in proliferating neurones | Reiner et al. Nature 1993. 364 |
| βIII-tubulin (Tuj-1) | Ab14545 AbCam | Typical of neuroblasts 1 and 2, in immature and mature neurons | Burgoyne R D, et al. EMBO J. 1998 |
| Ki67 | (Sp6) RM-9106-S1 NeoMarkers | Proliferation marker, present in proliferative early precursors and in neurosphere cells | Namiki J and Tator J. Neuropathol. Exp. Neurol. 1999 |

Example 4

Identification of the Surface Proteins Recognized by the NILO Antibodies

To identify the antigen recognized by the NILO antibodies immunoprecipitations of these antibodies has been carried out on neural progenitor cells to know the approximate size of been demonstrated that the interaction of antibodies with the neural stem cells derived from SVZ neurospheres from adults or OB of age 13.5 is capable of blocking the proliferation (FIG. 8) and differentiation (FIG. 9) processes of these cells to any of the three types of neural cells (neurones, oligodendrocytes or astrocytes).

Figure 8:
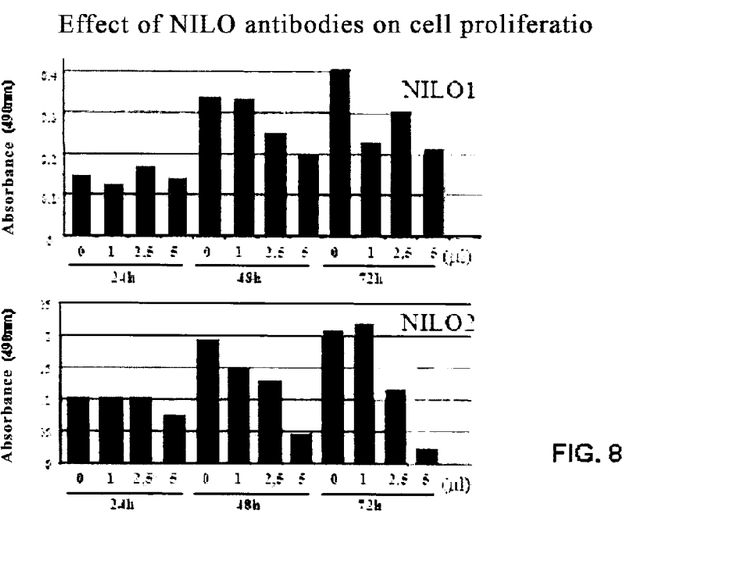
FIG. 8. Effect of NILO1 and NILO2 on neurosphere cell proliferation.
Figure 9:
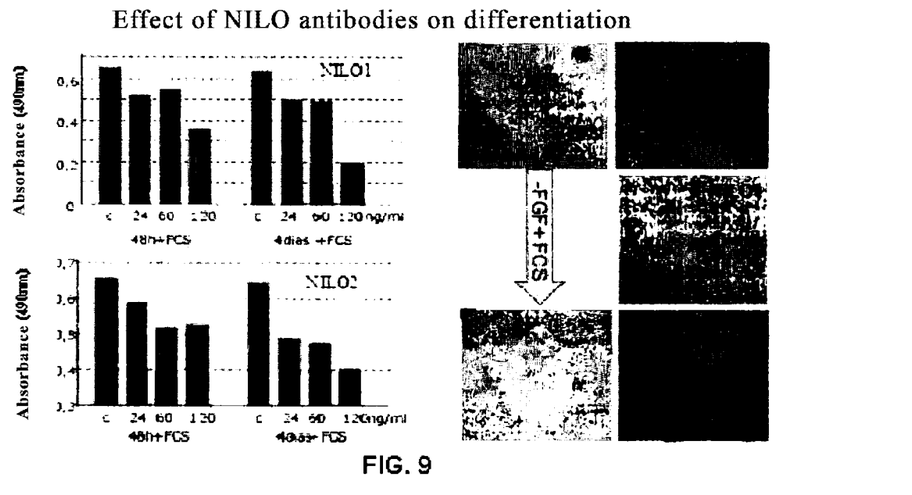
FIG. 9. Effect of NILO1 and NILO2 on the neurosphere cell differentiation.

Both NILO1 and NILO2 when added at different concentrations to neurospheres in culture media that enable their proliferation, halt said cell proliferation. In the continuous presence of the antibodies, the cells die after 5-6 days. All these data suggest that the NILO antibodies are recognizing receptors involved in the cell self-renewal processes or blocking the factors that maintain the self-renewal capacity (such as LIF or others) (FIG. 8).

When the neurosphere cells are placed in a differentiation medium in the absence of FGF2 and EGF, with or without 0.1% of fetal serum, and in the presence of different concentrations of purified NILO1, we have seen that the differentiation process is considerably reduced in comparison with the effect observed in the absence of antibody. NILO2 causes a similar effect on the differentiation of neurospheres although less marked than NILO1.

These data demonstrate that the continuous interaction of NILO with surface structures of neural progenitor cells generate important change in the behaviour of these cells, which suggests that the NILO antibodies are recognizing surface structures essential in the biology of these progenitor cells.

Example 6

Identification of Non-Neural Precursor Cells Identified by NILO1

The analysis of other tissues with the NILO monoclonal antibodies demonstrated that there are other minority populations outside the neural territory which are also marked with these antibodies. In particular, two populations of precursor cells which are identified with the NILO1 antibody are mesenchymal precursor cells of bone marrow and the precursor cells of breast tissue.

Figure 10:
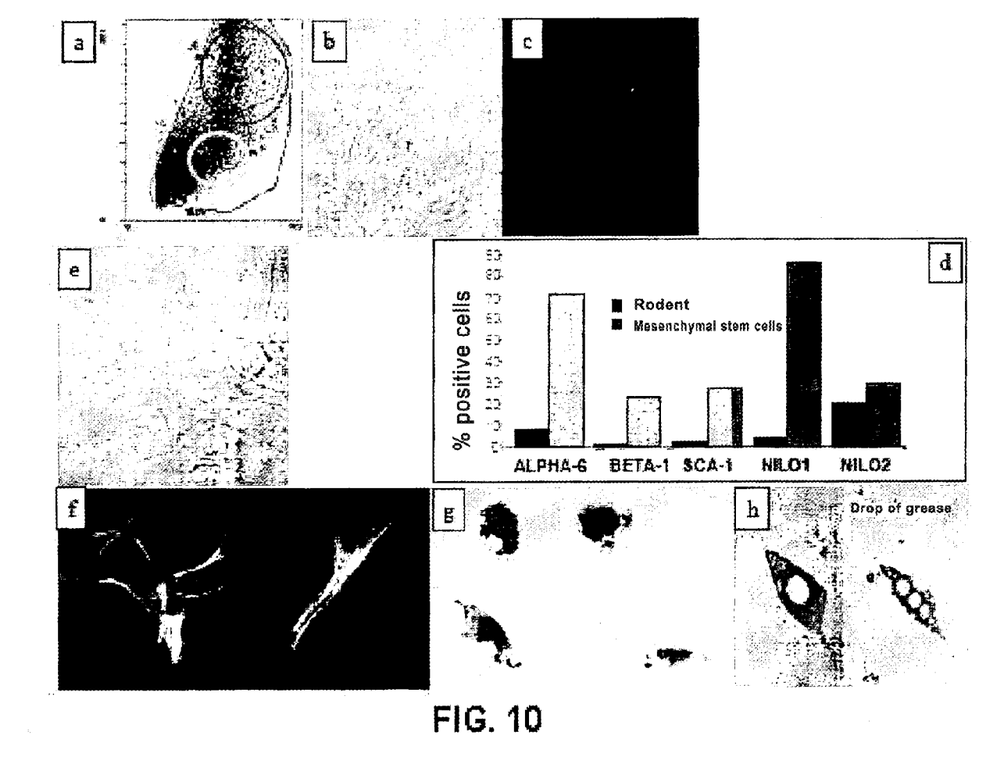
FIG. 10. NILO1 is capable of identifying mesenchymal precursor cells present in bone marrow.

A small percentage of cells marked with NILO1 in bone marrow and their possible involvement in their conversion with neural tissue in transplants in the brains of newborn mice were identified. Which type of cells was marked by NILO1 in bone marrow was investigated and analysed. Mesenchymal cells were prepared by means of adherence to the plastic in culture medium with fetal serum, resulting that the adherent cells and which lined the culture a few days after their sowing were positive for NILO1 (FIG. 10). These cells are considered mesenchymal since in neural tissue culture conditions (culture medium for growing neurospheres) these cells acquired nestin and NILO1 markers, as well as Sca-1, and the alpha6 and beta1 integrins. Furthermore, these markers are lost when they differentiated in the medium without FGF2 and EGF factors, towards βIII-tubulin+ cells, which would suggest their possible mesenchymal origin. Furthermore, for culture conditions in the differentiation of mesenchymal cells in adipocytes, these cells were capable in 6-week cultures of cells with grease (FIG. 10h) and marked with Red Oil (FIG. 10g), which demonstrates its capacity for generating various types of tissues derived from mesenchymal tissues.

Example 7

Identification of Breast Tissue Precursor Cells with NILO1

Figure 11:
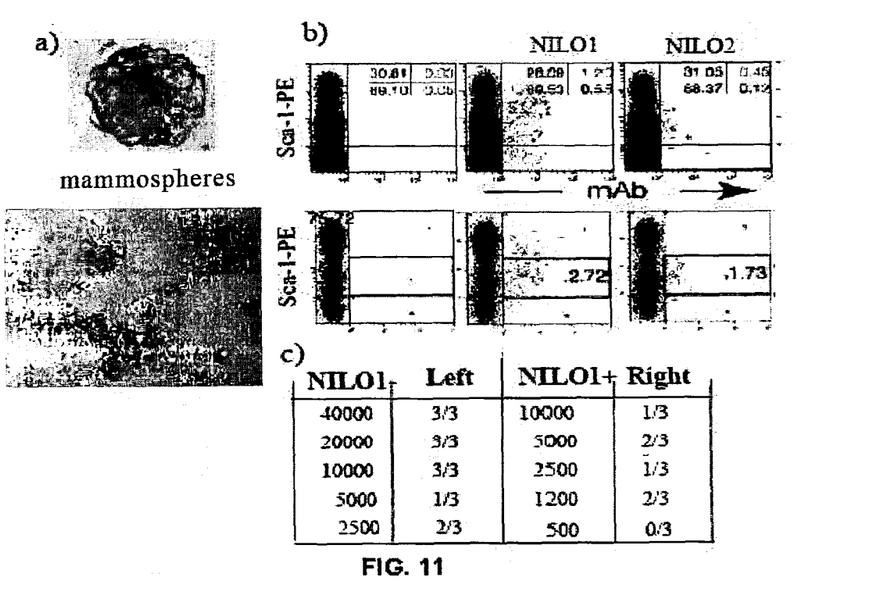
FIG. 11 NILO1 is capable of identifying breast tissue precursor cells.

In disaggregation conditions of the breast tissue of six week old mice, it has been observed that NILO1 is capable of identifying a small percentage of cells (<3%). These cells, capable of forming mammospheres, were weakly marked with Sca-1, which would suggest that they could be precursor cells (FIG. 11b). To demonstrate this point, disaggregated breast tissue cells were marked with the NILO1 antibody and they were separated in sterility, the NILO1+ and the NILO1- cells were then used in transplants of breast precursor tissue in the breast fat of laboratory mice and the presence of three-dimensional breast structures analysed 8 weeks post-transplant (FIG. 11c). As observed, 1200 cells of a selection of NILO1 cells by means of cytometry, were capable of reconstituting a three-dimensional breast. These data seem to show that NILO1 may recognize structure in breast tissue progenitor cells.

The invention claimed is:

1. A monoclonal antibody selected from among:
   a. a monoclonal antibody, NILO1, produced by the hybridoma deposited under the DSM access number No. ACC2887 in the international deposit authority Deutsche Sammlung von Mikroorganismen und Zellkulturen GmbH (DSMZ), Braunschweig, Germany; and
   b. a monoclonal antibody, NILO2, produced by the hybridoma deposited under the DSM access number No. ACC2881 in the international deposit authority Deutsche Sammlung von Mikroorganismen und Zellkulturen GmbH (DSMZ), Braunschweig, Germany;
   wherein the monoclonal antibody binds neurospheres that are positive for nestin, GFAP, and Ki67 or neural progenitor cells that are positive for doublecortin (DCX), Ki67, GFAP, Vimentin and beta III tubulin.

2. An antigen binding fragment of the monoclonal antibody of claim 1, wherein the antigen binding fragment is a F(ab), F(ab'), F(ab')$_2$, or Fv fragment and the anti en binding fragment binds neurospheres that are positive for nestin, GFAP positive, and Ki67 or neural progenitor cells that are positive for doublecortin (DCX), Ki67, GFAP, Vimentin and beta III tubulin.

3. A diabody, linear antibody, or single chain antibody comprising the antigen binding fragment of claim 2, wherein the diabody, linear antibody, or single chain antibody binds neurospheres that are positive for nestin, GFAP, and Ki67 or neural progenitor cells that are positive for doublecortin (DCX), Ki67, GFAP, Vimentin and beta III tubulin.

* * * * *